United States Patent
Chastain et al.

[11] Patent Number: 5,925,073
[45] Date of Patent: Jul. 20, 1999

[54] INTRAVENOUS CARDIAC LEAD WITH WAVE SHAPED FIXATION SEGMENT

[75] Inventors: Stuart R. Chastain, Shoreview; Bruce A. Tockman, Scandia; Randy W. Westlund, Minneapolis, all of Minn.

[73] Assignee: Cardiac Pacemakers, Inc., St. Paul, Minn.

[21] Appl. No.: 09/027,821

[22] Filed: Feb. 23, 1998

[51] Int. Cl.⁶ .................................................. A61N 1/05
[52] U.S. Cl. ........................ 607/122; 607/125; 607/126
[58] Field of Search ...................... 607/119, 122, 607/125, 126

[56] References Cited

U.S. PATENT DOCUMENTS

| | | |
|---|---|---|
| 5,387,233 | 2/1995 | Alferness . |
| 5,405,374 | 4/1995 | Stein . |
| 5,431,683 | 7/1995 | Bowald et al. . |
| 5,456,707 | 10/1995 | Giele . |
| 5,476,498 | 12/1995 | Ayers . |
| 5,683,445 | 11/1997 | Swoyer ...................................... 607/125 |
| 5,772,693 | 6/1998 | Brownlee .................................. 607/123 |
| 5,846,223 | 12/1998 | Swartz et al. ............................ 607/119 |

*Primary Examiner*—Francis J. Jaworski
*Assistant Examiner*—Carl H. Layno
*Attorney, Agent, or Firm*—Nikolai, Mersereau & Dietz, P.A.

[57] ABSTRACT

An intravenous lead for use with a cardiac device for implantation in the coronary venous system of the heart includes a lead body that is adapted to be routed through the vascular system into the coronary sinus with the distal end portion of the lead placed in the great cardiac vein or branch vein. The lead body includes a preformed section disposed just proximal of its tip so that the lead body exhibits a two-dimensional wave having peaks and valleys for contacting the endothelial layer of the vein at discrete, longitudinally spaced points to stabilize the electrode against displacement.

23 Claims, 3 Drawing Sheets

INTRAVENOUS CARDIAC LEAD WITH WAVE SHAPED FIXATION SEGMENT

BACKGROUND OF THE INVENTION

I. Field of the Invention

This invention relates generally to a cardiac pacing lead designed for placement in a coronary vein, and more particularly to such a lead employing a preformed shape in a distal end portion thereof for holding the distal end portion of the pacing lead carrying the stimulating electrode in place and for increased lead flexibility.

II. Discussion of the Prior Art

Cardiac pacemakers for treating bradycardia commonly employ pacing leads for connecting an electrical pulse generator to excitable cardiac tissue, usually within the heart's right ventricle. Such leads have one or more electrodes proximate the distal end thereof and also commonly employ tines located just distal of the tip electrode for holding that electrode in contact with endocardial tissue in the right ventricle. The tines engage the trabeculae, resisting movement of the lead tip due to body movement and/or contractions of the heart muscle itself.

More recently, researchers have found that cardiac stimulation can have a beneficial effect in treating patients suffering from congestive heart failure (CHF). By properly controlling the AV interval of the pacemaker, a sick heart may be made to pump more efficiently. Pacing therapy for the treatment of CHF, however, often requires the ability to stimulate the left ventricle, either alone or in conjunction with right ventricular stimulation. Current methods for achieving left ventricular pacing require placement of an epicardial lead, via thoracotomy or a thoracoscopic approach. Because of the usual poor condition of CHF patients, both of these procedures are "high risk" due to the trauma of the surgery itself and the need for general anesthesia. To obviate the need for a thoracotomy, left ventricular access (LVA) leads have been developed that may be introduced through the coronary sinus and then advanced through the coronary veins so that the lead's stimulating electrode can be positioned on the surface of the left ventricle near the apex of the heart.

Those skilled in the art knowing the anatomical configuration and dimensions of the coronary veins on the heart can appreciate that a lead to be routed therethrough must be of a relatively small diameter as compared to a conventional pacing lead adapted for placement in the right ventricle. Heart motion and respiratory motion as well as blood blow or other body movement are typical mechanisms for lead dislodgment. As such, a means must be provided for at least temporarily anchoring the electrode at a desired selected location until tissue ingrowth and resulting lead stabilization occurs. Additionally, a means must be provided to decouple the relative motion of the heart from the distal tip of the lead thereby reducing trauma to the coronary vein and neighboring myocardium. These problems are deemed to be more acute in CHF patients due to the dilated condition of CHF hearts and general diseased state of the tissue.

It can be seen, then, that a need exists for a pacing lead that can readily be advanced through the coronary sinus and thence through a coronary vein on the heart and having an anchoring and stress-relieving structure for safely maintaining the electrode at a desired site notwithstanding heart motion, respiratory motion blood flow and other body movement.

SUMMARY OF THE INVENTION

The present invention comprises an implantable lead for placement in a selected coronary vein. It includes a lead body with at least one electrode carried thereon at a distal end portion thereof and an elongated conductor contained within the lead body electrically joining a terminal pin at a proximal end of the lead body to the electrode at its distal end. To temporarily anchor the distal end portion of the lead body within the selected coronary vein until such time that tissue ingrowth can be relied upon for retention, the lead includes a distal end portion exhibiting a wave-like configuration with a plurality of longitudinally spaced peaks and valleys such that the lead body engages the vein wall at discrete points for inhibiting displacement of the electrode because of body movement, respiratory movement, beating action of the heart and flow of blood in the vein occupied by the lead. Additionally, the wave-like configuration adds resiliency to the lead body thereby reducing the dislodgment forces transmitted to the electrode and causing less injury to the vessel.

DESCRIPTION OF THE PREFERRED EMBODIMENT

Figure 1:
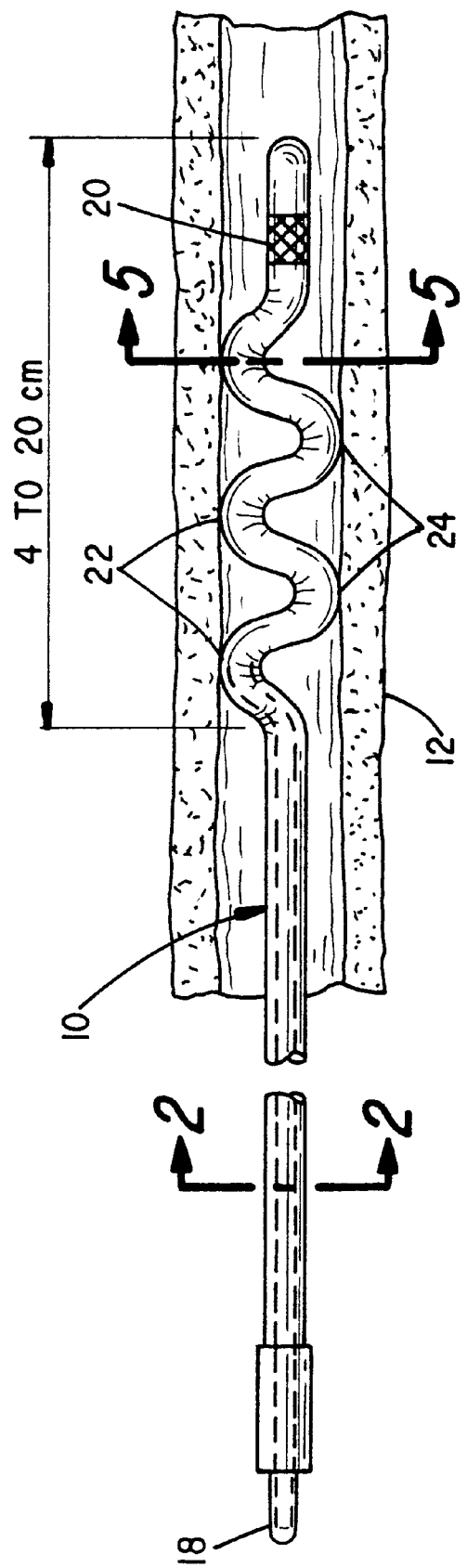
FIG. 1 is a side elevational view of a left coronary pacing lead, the distal end portion being shown within the lumen of a distal portion of coronary vein.
Figure 2:
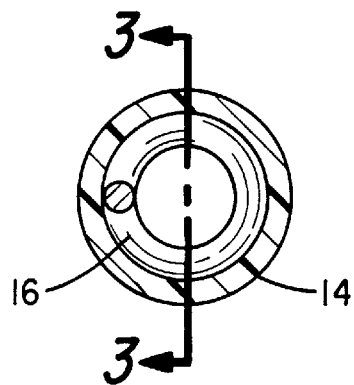
FIG. 2 is a cross-sectional view of the lead of FIG. 1 taken along the line 2—2 in FIG. 1.
Figure 3:
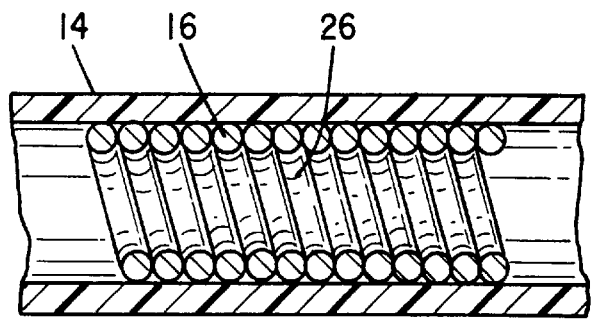
FIG. 3 is a cross-sectional view taken along the line 3—3 in FIG. 2.

Referring to FIG. 1, there is indicated generally by numeral 10 a pacing lead specifically designed to be routed through the coronary sinus and into the great cardiac vein or branch vein, traversing the epicardium of the left ventricle. A segment of vein is identified by numeral 12. The lead preferably comprises an elongated flexible outer insulating polymer jacket 14 that surrounds an inner, helically wound conductor 16. The conductor 16 extends the full length of the lead from its proximal terminal pin 18 to an electrode 20 affixed near the distal end of the lead body.

In accordance with the present invention, a portion of the lead body located just proximal of the distal electrode 20 is preformed to exhibit a wave-like appearance defining a plurality of peaks 22 and valleys 24 which lie substantially in one plane. With no limitation intended, the outer jacket 14 of the lead body may have a O.D. in the range of from about 3 Fr to 5 Fr (0.039–0.065 in.) and the wave-like portion may be located proximally from the lead tip and may span a zone about 4–7 centimeters in length. The peak-to-peak amplitude of the undulations in the lead body might typically be in a range of from 0.5–4.0 centimeters.

The amplitude and frequency of the wave shape is intended to cause the lead 10 to make intermittent contact with the wall of the vein 12. The force exerted on the vessel wall by the built-in bias property provides resistance to extraction forces attributable to heart motion, respiratory motion and blood flow in the vasculature. The resiliency imparted to the lead by the wave shape absorbs heart and respiratory motion forces, thereby decoupling the mechanisms of dislodgement from the distal end of the lead. Both attributes of the built-in bias act to stabilize the electrode in its initial implant position without injury or damage to the vessel or underlying myocardium.

The wave-like shape may be imparted to the lead by preforming the conductor coil 16 prior to the application of the polymer jacket 14 so that when the lead is unconstrained, the distal end portion will assume the wave-like configuration. Alternatively, the bias may be imparted to the lead in a zone near its distal end by selective molding of the insulating polymer jacket 14 over the coiled conductor 16.

With the conductor 16 being helically wound, it defines an internal lumen 26. The shape-biased lead is preferably implanted by tracking over a guidewire passed through the tubular terminal pin 18 and through the lumen 26 of the lead body. The guidewire overcomes the bias built into the lead and effectively straightens out the wave comprising the retention portion of the lead as it is being routed through the vascular system, the coronary sinus and into the great cardiac vein and branch vein. Alternatively, a stiff stylet may be used to straighten out the bias for routing through the coronary vascular system. Once the electrode 20 is positioned at a desired site, the guidewire or stiffening stylet is withdrawn, allowing the built-in bias to restore the wave-like shape to the anchoring portion of the lead so that it will engage the walls of the coronary vein at each peak and valley.

Figure 4:
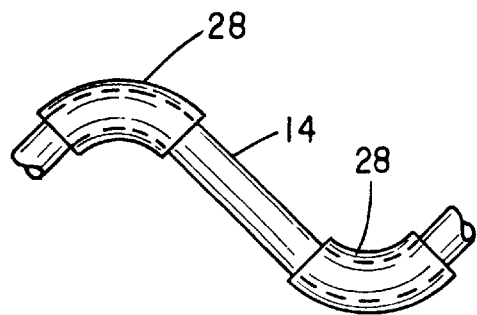
FIG. 4 is a greatly enlarged view of a segment of the distal end portion of the lead of FIG. 1.

An enhancement of the above-described concept is illustrated in FIG. 4. Here, a stiffening element 28 is added at discrete, spaced-apart locations within the wave-like shape imparted to the lead body. The stiffening elements 28 are disposed on the helical wound conductor and may be composed of, for example, thin-walled heat shrink PTFE tubing. These tubing segments 28 increase the contact force between the lead body and the blood vessel wall 12, causing the reinforced bends to function as anchoring points as previously described while other bends not reinforced with the shrink-tubing function to decouple movements of the lead body from displacing the electrode 20 from its desired stimulating site.

Figure 5:
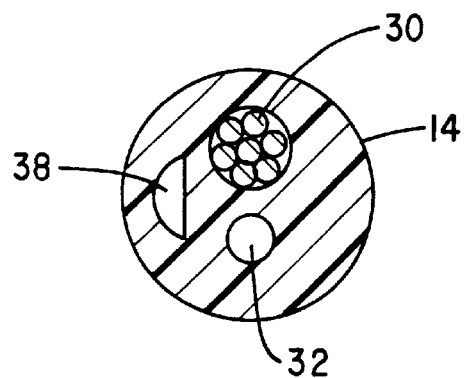
FIG. 5 is a cross-sectional view taken along line 5—5 in FIG. 1 showing an alternative lead construction.
Figure 6:
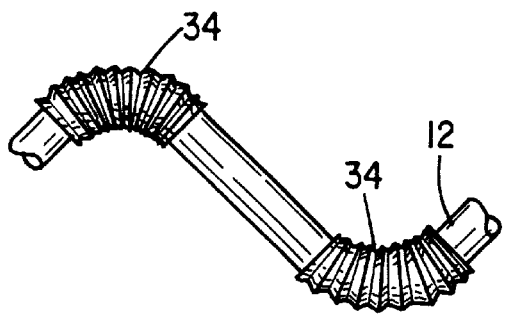
FIG. 6 is a greatly enlarged view of a segment of the distal end portion of the lead of FIG. 1 incorporating an external shaping member.
Figure 7:
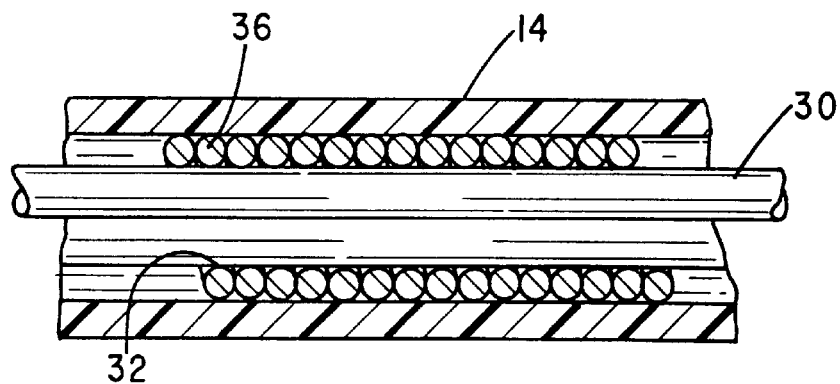
FIG. 7 is an enlarged longitudinal cross-sectional view of a portion of the lead body with an internal shaping member.

A further embodiment of the present invention is shown in FIG. 5 and comprises a lead having a braided cable conductor with an adjacent lumen 32 extending along side it from the distal tip to the terminal pin and of sufficient size to accept a guidewire or stiffening stylet therein. Wave-like shapes can be imparted to such a lead by means of pre-molded portions of the lead body as previously explained with the aid of FIG. 4 by including shaping elements within the lead body, such as an external shaping coil as at 34 in FIG. 6 or an internal shaping coil as at 36 in FIG. 7 or even a premolded polymer shaping element as at 38 in FIG. 5.

A distinct advantage of the present invention resides in the intermittent points of the contact between the lead body and the vessel wall. This offers an advantage over prior art coronary sinus leads, such as that described in the Ayers U.S. Pat. No. 5,476,498. The Ayers lead has a helical bias that places the lead body in substantial contact with the wall of the great cardiac vein or coronary sinus over the length of the helix. Experiments have shown that a lead in contact with the vessel wall elicits a histological response that encapsulates and attaches the lead to the endothelial wall of the blood vessel in which it is placed. The helical fixation places a substantial surface in contact and greatly complicates any chance of using standard removal techniques should it become necessary to explant the lead. In dog experiments which have been conducted, it has been demonstrated that a "saw-tooth" wave bias tends only to elicit encapsulation at the intermittent points of contact with the vessel wall, thereby reducing the degree of involvement and, hence, facilitating lead removal following histological maturation.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A pacing lead for a cardiac stimulator comprising:
   an elongated, flexible insulating lead body having a proximal end, a distal end and a lumen extending therebetween with an electrode attached to the lead body at the distal end and a terminal pin attached to the proximal end, the lead body including an elongated conductor disposed in the lumen for connecting the electrode to the terminal pin, the lead body dimensioned to be passed through the coronary sinus vein and into a branch of the great coronary vein, the lead body having a zone with a preformed shape configuration immediately proximal to the electrode, the preformed shape being a wave exhibiting a series of peaks and valleys for engaging a wall of the great coronary vein branch at a predetermined number of discrete, longitudinally spaced points for holding the electrode relatively fixed in position irrespective of forces due to body movements and blood flow in the coronary vein and coronary sinus vein and for decoupling said forces from the lead tip.

2. The lead as in claim 1 wherein the series of peaks and valleys lie in a single plane.

3. The lead as in claim 1 wherein the elongated conductor is helically wound and has an open center.

4. The lead as in claim 3 wherein the open center of the helically wound conductor is of a size to receive a straightening member therein.

5. The lead as in claim 1 or 2 wherein the peaks and valleys are located over a length from about 4 to 20 centimeters proximally of the electrode.

6. The lead as in claim 1 wherein the wave has an amplitude in a range from about 0.5 to 4.0 centimeters, peak-to-peak.

7. The lead as in claim 1 wherein the lead body includes a polymer jacket having a biasing means for imparting the preformed shape.

8. The lead as in any one of claims 1 or 2 through 5 wherein an outer diameter of the lead body is in a range from about 3 Fr to 5 Fr.

9. The lead as in claim 1 or 2 and further including means located at the peaks and valleys for imparting a shape bias thereat.

10. The lead as in claim 9 wherein the means for imparting a shape bias comprises discrete segments of heat shrinkable tubing disposed about the lead body.

11. The lead as in claim 9 wherein the means for imparting a shape bias comprises a shaping coil disposed along a predetermined portion of the lead body.

12. The lead as in claim 9 wherein the means for imparting a shape bias comprises at least one premolded polymer element disposed along a predetermined portion of the lead body.

13. The lead as in claim 1 and further including a second lumen in the lead body extending between the proximal end and distal end thereof.

14. The lead as in claim 13 wherein the conductor comprises a braided cable.

15. The lead as in claim 14 wherein the preformed shape comprises a wave exhibiting a series of peaks and valleys.

16. The lead as in claim 13 wherein the second lumen is of a size to receive a straightening member therein.

17. The lead as in claim 14 wherein the lead body includes a polymer jacket having biasing means for imparting the preformed shape.

18. The lead as in claim 15 and further including means located at the peaks and valleys for imparting a shape bias thereat.

19. The lead as in claim 18 wherein the means for imparting the shape bias comprises a shaping coil disposed in the zone.

20. The lead as in claim 18 wherein the means for imparting a shape bias comprises a premolded polymer element disposed on said lead body.

21. The lead as in any one of claims 13–15 or 16 wherein the zone extends over a length from about 4 to 20 centimeters proximally of the electrode.

22. The lead as in any one of claims 13–15 or 16 wherein an outer diameter of the lead body is in a range from 3 Fr to 5 Fr.

23. The lead as in any one of claims 15 or 16 wherein the wave has an amplitude in a range of from about 0.5 to 4.0 centimeters, peak-to-peak.

* * * * *

(12) EX PARTE REEXAMINATION CERTIFICATE (7165th)
United States Patent
Chastain et al.

(10) Number: US 5,925,073 C1
(45) Certificate Issued: Nov. 17, 2009

(54) INTRAVENOUS CARDIAC LEAD WITH WAVE SHAPED FIXATION SEGMENT

(75) Inventors: Stuart R. Chastain, Shoreview, MN (US); Bruce A. Tockman, Scandia, MN (US); Randy W. Westlund, Minneapolis, MN (US)

(73) Assignee: Cardiac Pacemakers, Inc., St. Paul, MN (US)

Reexamination Request:
No. 90/007,264, Oct. 22, 2004

Reexamination Certificate for:
Patent No.: 5,925,073
Issued: Jul. 20, 1999
Appl. No.: 09/027,821
Filed: Feb. 23, 1998

(51) Int. Cl.
*A61N 1/05* (2006.01)

(52) U.S. Cl. .................. 607/122; 607/125; 607/126
(58) Field of Classification Search .................. None
See application file for complete search history.

(56) References Cited

U.S. PATENT DOCUMENTS

| | | |
|---|---|---|
| 3,769,984 A | 11/1973 | Muench |
| 4,011,875 A | 3/1977 | Lehr et al. |
| 4,106,512 A | 8/1978 | Bisping |
| 4,146,036 A | 3/1979 | Dutcher et al. |
| 4,185,639 A | 1/1980 | Linder |
| 4,217,913 A | 8/1980 | Dutcher |
| 4,282,885 A | 8/1981 | Bisping |
| 4,311,153 A | 1/1982 | Smits |
| 4,340,091 A * | 7/1982 | Skelton et al. .......... 139/383 R |
| 4,355,646 A | 10/1982 | Kallok et al. |
| 4,374,527 A | 2/1983 | Iversen |
| 4,667,686 A | 5/1987 | Peers-Travarton |
| 4,932,407 A | 6/1990 | Williams |
| 4,934,381 A | 6/1990 | MacGregor |
| 5,003,990 A | 4/1991 | Osypka |
| 5,014,696 A | 5/1991 | Mehra |
| 5,016,646 A | 5/1991 | Gotthardt et al. |
| 5,099,838 A | 3/1992 | Bardy |
| 5,103,837 A | 4/1992 | Weidlich et al. |
| 5,304,218 A | 4/1994 | Alferness |
| 5,313,943 A | 5/1994 | Houser et al. |
| 5,324,324 A | 6/1994 | Vachon et al. |
| 5,348,021 A | 9/1994 | Adams et al. |
| 5,350,404 A | 9/1994 | Adams et al. |
| 5,381,790 A | 1/1995 | Kanesaka |
| 5,387,233 A | 2/1995 | Alferness |
| 5,405,374 A | 4/1995 | Stein |
| 5,431,683 A | 7/1995 | Bowald et al. |
| 5,433,729 A | 7/1995 | Adams et al. |
| 5,456,707 A | 10/1995 | Giele |
| 5,458,621 A | 10/1995 | White et al. |
| 5,476,498 A | 12/1995 | Ayers |
| 5,487,385 A | 1/1996 | Avitall |

(Continued)

FOREIGN PATENT DOCUMENTS

| | | |
|---|---|---|
| EP | 0 057 877 B1 | 8/1982 |
| EP | 0 057 877 A1 | 8/1992 |
| EP | 0 709 111 A2 | 5/1996 |
| EP | 0 709 111 A3 | 11/1997 |
| GB | 2 032 278 A | 5/1980 |

OTHER PUBLICATIONS

Research Disclosure, "Guidewire Placement of Electric Lead," Oct. 1993, p. 685.

Advances in Pacemaker Technology (M. Schaldach et al. eds., Springer–Verlag, 1975) pp. 30–31.

*Primary Examiner*—Cary E. O'Connor

(57) ABSTRACT

An intravenous lead for use with a cardiac device for implantation in the coronary venous system of the heart includes a lead body that is adapted to be routed through the vascular system into the coronary sinus with the distal end portion of the lead placed in the great cardiac vein or branch vein. The lead body includes a preformed section disposed just proximal of its tip so that the lead body exhibits a two-dimensional wave having peaks and valleys for contacting the endothelial layer of the vein at discrete, longitudinally spaced points to stabilize the electrode against displacement.

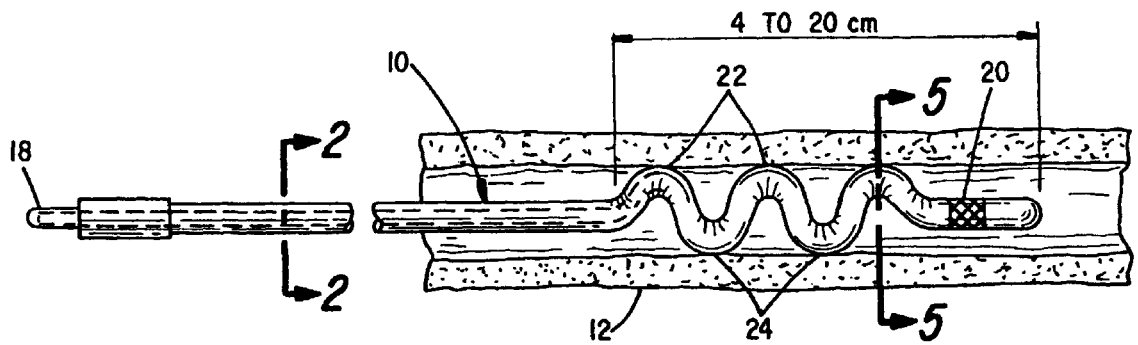

U.S. PATENT DOCUMENTS

| | | |
|---|---|---|
| 5,514,173 A | 5/1996 | Rebell et al. |
| 5,520,194 A | 5/1996 | Miyata et al. |
| 5,545,204 A | 8/1996 | Cammilli et al. |
| 5,573,039 A * | 11/1996 | Mang .................. 138/141 |
| 5,584,873 A | 12/1996 | Shoberg et al. |
| 5,609,622 A | 3/1997 | Soukup et al. |
| 5,643,231 A | 7/1997 | Lurie et al. |
| 5,683,445 A | 11/1997 | Swoyer |
| 5,755,659 A * | 5/1998 | Zurbrugg .................. 600/36 |
| 5,755,765 A | 5/1998 | Hyde et al. |
| 5,755,766 A | 5/1998 | Chastain et al. |
| 5,772,693 A | 6/1998 | Brownlee |
| 5,782,239 A | 7/1998 | Webster, Jr. |
| 5,782,760 A | 7/1998 | Schaer |
| 5,800,495 A | 9/1998 | Machek et al. |
| 5,846,223 A | 12/1998 | Swartz et al. |
| 5,897,819 A | 4/1999 | Miyata et al. |
| 5,910,364 A | 6/1999 | Miyata et al. |
| 5,922,014 A | 7/1999 | Warman et al. |
| 5,957,842 A | 9/1999 | Littmann et al. |
| 6,141,576 A | 10/2000 | Littmann et al. |

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–23 are cancelled.

* * * * *